US007824868B2

(12) United States Patent
Höök et al.

(10) Patent No.: US 7,824,868 B2
(45) Date of Patent: Nov. 2, 2010

(54) FORMATION OF SUPERFIBRONECTIN BY BBK32 AND USES THEREFOR

(76) Inventors: Magnus Höök, 4235 Oberlin, Houston, TX (US) 77005; Sabitha Prabhakaran, 4410 Leyland Dr., Pearland, TX (US) 77584

( * ) Notice: Subject to any disclaimer, the term of this patent is extended or adjusted under 35 U.S.C. 154(b) by 126 days.

(21) Appl. No.: 12/148,389

(22) Filed: Apr. 18, 2008

(65) Prior Publication Data

US 2009/0170751 A1 Jul. 2, 2009

Related U.S. Application Data

(60) Provisional application No. 60/925,341, filed on Apr. 19, 2007.

(51) Int. Cl.
*G01N 33/55* (2006.01)
*A61K 38/16* (2006.01)

(52) U.S. Cl. ........................................... 435/7.1; 514/8

(58) Field of Classification Search ....................... None
See application file for complete search history.

(56) References Cited

OTHER PUBLICATIONS

Prabhakaran et al., "A Novel Fibronectin Binding Motif in MSCRAMMs Targets F3 Modules", PloS ONE, vol. 4, No. 4, p. e5412 (pp. 1-10).*

* cited by examiner

*Primary Examiner*—Suzanne M. Noakes
(74) *Attorney, Agent, or Firm*—Benjamin Aaron Adler (57) ABSTRACT

Provided herein is a method for inducing formation of a conformationally distinct superfibronectin by contacting plasma fibronectin with BBK32 protein or a BBK32 peptide and the BBK32-induced superfibronectin so formed. Also provided are methods of inhibiting endothelial cell proliferation, of treating pathophysiological conditions associated with endothelial cell proliferation and of inhibiting angiogenesis therein using the BBK32 protein, BBK32 peptide or the BBK32-induced superfibronectin.

8 Claims, 5 Drawing Sheets
(1 of 5 Drawing Sheet(s) Filed in Color)

FORMATION OF SUPERFIBRONECTIN BY BBK32 AND USES THEREFOR

CROSS REFERENCE TO RELATED APPLICATION

This non-provisional application claims benefit of provisional application U.S. Ser. No. 60/925,341 filed on Apr. 19, 2007, now abandoned.

FEDERAL FUNDING LEGEND

This invention was produced in part using funds obtained through grants AI058086 and AI020624 from the National Institutes of Health. Consequently, the federal government has certain rights in this invention.

BACKGROUND OF THE INVENTION

1. Field of the Invention

The present invention relates to the fields of protein molecular biology and pathogenic microbiology. More specifically, the present invention relates to BBK32 peptides effective to induce superfibronectin aggregation and uses to treat endothelial cell proliferative-associated diseases or disorders.

2. Description of the Related Art

*Borrelia burgdorferi* sensu lato is the causative agent of borrelioses such as Lyme disease, the most common arthropod-borne infectious disease in North America and Europe (1). *B. burgdorferi* has a complicated life cycle and oscillates between ticks and vertebrate hosts. The molecular pathogenesis of Lyme disease is unclear especially since *Borrelia* does not produce any known virulence determinants or toxins that share homology with other pathogens. It has been suggested that the various lipoproteins on the outer membrane sheath allow the spirochete to interact with host tissues and likely play key roles in the infectious process (2).

Transcriptional analyses of *B. burgdorferi* under different conditions suggest that a set of 11 lipoproteins are selectively upregulated when the spirochete is exposed to a mammalian host (3). BBK32, a fibronectin-binding 47 kDa MSCRAMM (Microbial Surface Components Recognizing Adhesive Matrix Molecule), is one of the upregulated lipoproteins. It was originally identified as a fibronectin-binding MSCRAMM by probing lysates of *B. burgdorferi* with fibronectin in Far Western blots (2). BBK32 was localized to the surface of the spirochete and the attachment of *B. burgdorferi* to fibronectin substrates was blocked by addition of soluble recombinant BBK32 protein suggesting that BBK32 is the primary fibronectin-binding adhesin on *B. burgdorferi* sensu stricto (2).

Orthologous genes are found in the closely related species, *B. garinii* and *B. afzelii* (4). Expression of BBK32 at the site of experimental infection in mice increases from days 3 to 7 and then declines, but bbk32 gene expression can be detected in the skin, heart, spleen, joints and bladder at least 30 days post challenge, indicating that the lipoprotein is expressed by the spirochete as it disseminates to different tissues in the host (3). *B. burgdorferi* mutant strains containing bbk32 deletions have an attenuated infectivity when assessed at twenty-one days post infection (5) demonstrating that BBK32 is a virulence factor in borrelioses.

The N-terminus of BBK32 contains a signal peptide followed by a "lipobox" and an extended disordered segment, residues 21-205, that contains the fibronectin-binding sites (6). The C-terminal part of the protein (residues 206-354) appears as a globular domain that may bind fibrinogen (6). Upon binding to the N-terminal segment of fibronectin, the ligand binding segment of BBK32 undergoes conformational changes to form beta-strands that complement existing beta-sheets in fibronectin modules. This binding mechanism called the Tandem Beta-Zipper mechanism (6-7) has previously been demonstrated for the interaction of fibronectin with MSCRAMMs from *Staphylococcus aureus* and *Streptococcus pyogenes* (8).

Fibronectin is a large dimeric glycoprotein found in a soluble form in plasma and other body fluids and in the insoluble fibrillar form in the extracellular matrix. This dynamic protein plays key roles in basic physiological processes such as cell proliferation, migration, and survival by interacting with a variety of extracellular macromolecules and cellular receptors, primarily of the integrin family (9). Fibronectin is composed of three types of repeating modules: 12 type I modules ($F_1$), 2 type II modules ($F_2$), and 15-17 (dependent on alternative splicing) type III modules ($F_3$), and an alternatively spliced variable sequence that is not homologous to other parts of fibronectin. $F_1$ and $F_2$ modules are stabilized by disulfide bonds whereas $F_3$ modules lack disulfide bonds and can reversibly partially unfold (10-11). The two monomers are connected at the C-termini by two disulfide bonds.

Soluble fibronectin adopts a somewhat compact form that is stabilized by intramolecular ionic interactions between specific modules. The interactions occur primarily between the $^1F_1$-$^5F_1$, the $^2F_3$-$^3F_3$, and $^{12}F_3$-$^{14}F_3$ segments (12). In the extracellular matrix fibronectin takes on a more extended form and the protein is likely engaged in multiple intra- and intermolecular interactions (13), but the structural organizations of fibronectin matrices have not been elucidated in detail. It is likely that the incorporation of soluble fibronectin into a matrix involves a complex but orderly breaking of intramolecular bonds in the compact soluble fibronectin and the formation of new intra- and intermolecular interactions whereby an extended form of fibronectin is deposited in a matrix. This process is facilitated by integrins and other cellular components (14-15). The fibronectin-binding MSCRAMM Sfb1 from *S. pyogenes* apparently can interfere in this process and inhibits fibronectin matrix formation in fibroblast cultures (16).

Fibronectin may occur in different aggregated forms. "Superfibronectin" (sFn) is a form of fibronectin aggregates that resembles matrix fibronectin but has distinctly different biological activities (17). Superfibronectin is formed by mixing plasma fibronectin with Anastellin, a recombinant form of the C-terminal two-thirds of $^1F_3$. $F_3$ modules are beta-sandwiches composed of a quadruple-stranded beta-sheet and a triple-stranded beta-sheet. In Anastellin, strands A and B are removed, exposing the E and C strands. This exposure is perhaps responsible for Anastellin's self-association and interaction with other fibronectin modules (18) ($^1F_1$-$^5F_1$, gelatin binding domain, $F_3$ modules). These interactions lead to the formation of sFn. Ohashi and Erickson recently suggested a model of sFn formation whereby Anastellin binds to partially unfolded $F_3$ modules and prevents refolding, thus exposing hydrophobic surfaces and beta-sheet edges. The exposed elements bind to similar exposed elements on other fibronectin molecules leading to a specific ordered aggregation (19).

A large number of pathogenic microorganisms have been shown to express fibronectin-binding MSCRAMMs although only a few of these interactions have been characterized in detail. The *S. aureus* fibronectin-binding MSCRAMM FnbpA is composed of 11 repeats that each may bind to the N-terminal $^1F_1$-$^5F_1$ segment of fibronectin (8). Sfb1 from *S. pyogenes* also contains repeats that bind to the N-terminal $F_1$ modules. However, this MSCRAMM also interacts with the gelatin binding domain of fibronectin composed of $^6F_1{}^1F_2{}^2F_2{}^7F_2{}^8F_1{}^9F_1$ (20). In mapping the binding sites in fibronectin for BBK32, it was determined that the MSCRAMM not only binds to the N-terminal domain and the gelatin binding domain but also the $^1F_3$, $^{1-2}F_3$, and $^3F_3$ modules.

Thus, a recognized need is present in the art for alternate methods of inducing superfibronectin aggregation. Specifically, the prior art is deficient in methods of inducing superfibronectin aggregation by contacting fibronectin with BBK32 peptides and in methods of using BBK32-induced superfibronectin aggregates for treating endothelial cell proliferative-associated pathophysiological conditions. The present invention fulfils this longstanding need in the art.

SUMMARY OF THE INVENTION

The present invention is directed to a method for inducing formation of a superfibronectin. The method comprises contacting plasma fibronectin with BBK32 protein or a peptide therefrom where binding of the BBK32 protein or peptide to the plasma fibronectin induces a conformational change therein thereby forming the superfibronectin. The BBK32 peptides may be $BBK32_{(21-205)}$, $BBK32_{(21-354)}$, $BBK32_{(146-166)}$, $BBK32_{(153-166)}$, $BBK32_{(153-175)}$, $BBK32_{(160-186)}$, or $BBK32_{(175-202)}$. The present invention is directed to a related method comprising a further method step of inhibiting proliferation of endothelial cells with the BBK32 peptides. The present invention is directed to another related method comprising a further method step of isolating the BBK32-induced superfibronectin.

The present invention is directed to an isolated and purified BBK32-induced superfibronectin formed by the methods described herein. The present invention also is directed to a related method for inhibiting proliferation of endothelial cells associated with a pathophysiological condition. The method comprises contacting the endothelial cells with the isolated and purified BBK32-induced superfibronectin described herein.

The present invention is directed further to a method for treating a pathophysiological condition associated with endothelial cell proliferation in a subject. The method comprises administering a pharmacologically effective amount of BBK32 protein or of the BBK32 peptides described herein to the subject. Binding of the BBK32 protein or BBK32 peptide to fibronectin induces the formation of a superfibronectin effective to inhibit proliferation of endothelial cells thereby treating the condition.

The present invention is directed further still to a related method for treating a pathophysiological condition associated with endothelial cell proliferation in a subject. The method comprises administering to the subject a pharmacologically effective amount of an isolated superfibronectin induced to form by binding of BBK32 protein or a BBK32 peptide to plasma fibronectin. The isolated superfibronectin effective to inhibit proliferation of endothelial cells thereby treating the condition.

The present invention is directed further still a method for inhibiting angiogenesis occurring in a pathophysiological condition associated with endothelial cell proliferation in a subject. The method comprises administering to the subject an amount of a BBK32 protein, a BBK32 peptide or a BBK32-induced superfibronectin described herein that is pharmacologically effective to induce an antiangiogenetic response thereby inhibiting angiogenesis in the pathophysiological condition.

Other and further aspects, features, benefits, and advantages of the present invention will be apparent from the following description of the presently preferred embodiments of the invention given for the purpose of disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 4A-4B illustrate the effects of $BBK32_{(21-205)}$ on NHDFs. FIG. 4A shows that $BBK32_{(21-205)}$ co-localizes with fibronectin on NHDFs. Cells were allowed to grow for 48 hours and then 5 µM $BBK32_{(21-205)}$ or 5 µM Anastellin was added in fresh media. Cells were treated for 20 hours and then fixed. Following blocking with BSA, anti-fibronectin conjugated to Alexa Fluor 488 and anti-His conjugated to Texas Red were used to probe for the presence of fibronectin and $BBK32_{(21-205)}$ and Anastellin, respectively. FIG. 4B shows that $BBK32_{(21-205)}$ affects matrix assembly on NHDFs. Cells were allowed to grow for 48 hours and then were incubated with 5 mM $BBK32_{(21-205)}$, 5 µM Anastellin, or 5 µM FnbpA peptide D3. Treated cells were incubated for 20 hours and probed with Alexa Fluor 488-anti-fibronectin, monoclonal antibody IST-1, and monoclonal antibody IST-9. Images were taken using LSM 510 Confocal Microscope. Bar=10 μm.

DETAILED DESCRIPTION OF THE INVENTION

In one embodiment of the present invention there is provided a method for inducing formation of a superfibronectin, comprising contacting plasma fibronectin with BBK32 protein or a peptide therefrom wherein binding of the BBK32 protein or peptide to the plasma fibronectin induces a conformational change therein thereby forming the superfibronectin.

Further to this embodiment the method may comprise inhibiting proliferation of endothelial cells. In this further embodiment, inhibiting proliferation of the endothelial cells may inhibit angiogenesis. Also, in this further embodiment, the endothelial cells may be associated with an endothelial cell proliferative pathophysiological condition. Examples of the cell proliferative pathophysiological condition are a borreliosis, a neoplastic disease, stent restinosis, diabetic retinopathy, or a wound. A particular example of a borreliosis is Lyme disease. In another further embodiment the method may comprise isolating the BBK32-induced superfibronectin.

In all embodiments, the BBK32-induced superfibronectin is conformationally distinct from plasma fibronectin and matrix fibronectin. Also in all embodiments the BBK32 peptide may include one or more sequential residues from the antiproliferation active site of the BBK32 protein. Particularly the antiproliferation active site includes residues 146 to 175. Examples of the BBK32 peptide are $BBK32_{(21-205)}$, $BBK32_{(146-166)}$, $BBK32_{(153-166)}$, $BBK32_{(153-175)}$, $BBK32_{(160-186)}$, or $BBK32_{(175-202)}$.

In another embodiment of the present invention there is provided an isolated and purified BBK32-induced superfibronectin formed by the method described supra. This embodiment also provides a pharmaceutical composition comprising the BBK32-induced superfibronectin and a pharmaceutically acceptable carrier.

In a related embodiment there is provided a method for inhibiting proliferation of endothelial cells associated with a pathopysiological condition, comprising contacting the endothelial cells with the isolated and purified BBK32-induced superfibronectin described herein. In this related embodiment the BBK32-induced superfibronectin may inhibit angiogenesis in the pathophysiological condition. The BBK32 peptides and the pathopysiological condition may be as described supra.

In yet another embodiment of the present invention there is provided a method for treating a pathophysiological condition associated with endothelial cell proliferation in a subject, comprising administering a pharmacologically effective amount of BBK32 protein or of a BBK32 peptide to the subject, wherein binding of the BBK32 protein or BBK32 peptide to fibronectin induces the formation of a superfibronectin effective to inhibit proliferation of endothelial cells thereby treating the condition. In this embodiment the BBK32-induced superfibronectin inhibits angiogenesis in the pathophysiological condition. The BBK32 peptides and the pathopysiological condition may be as described supra.

In yet another embodiment of the present invention there is provided a method for treating a pathophysiological condition associated with endothelial cell proliferation in a subject, comprising administering to the subject a pharmacologically effective amount of an isolated superfibronectin induced to form by binding of BBK32 protein or a BBK32 peptide to plasma fibronectin, said isolated superfibronectin effective to inhibit proliferation of endothelial cells thereby treating the condition.

In this embodiment the BBK32-induced superfibronectin is conformationally distinct from plasma fibronectin and matrix fibronectin. Also, the BBK32-induced superfibronectin inhibits angiogenesis in the pathophysiological condition. In addition the BBK32 peptide effective to induce superfibronectin formation includes one or more sequential residues from the antiproliferation active site of the BBK32 protein which is residues 146-175. The BBK32 peptides may be $BBK32_{(21-205)}$, $BBK32_{(21-354)}$, $BBK32_{(146-166)}$, $BBK32_{(153-166)}$, $BBK32_{(153-175)}$, $BBK32_{(160-186)}$, or $BBK32_{(175-202)}$. In addition, the pathophysiological condition associated with endothelial cell proliferation is as described.

In yet another embodiment of the present invention there is provided a method for inhibiting angiogenesis occurring in a pathophysiological condition associated with endothelial cell proliferation in a subject, comprising administering to the subject an amount of a BBK32 protein, a BBK32 peptide or a BBK32-induced superfibronectin pharmacologically effective to induce an antiangiogenetic response thereby inhibiting angiogenesis in the pathophysiological condition. The BBK32 peptides, the BBK32-induced superfibronectin and the pathophysiological conditions are as described supra.

As used herein, the term "a" or "an" when used in conjunction with the term "comprising" in the claims and/or the specification may mean "one," but it is also consistent with the meaning of "one or more," "at least one," and "one or more than one." As used herein, the term "or" in the claims is used to mean "and/or" unless explicitly indicated to refer to alternatives only or the alternatives are mutually exclusive, although the disclosure supports a definition that refers to only alternatives and "and/or."

As used herein, the term "contacting" refers to any suitable method of bringing a BBK32 protein or BBK32 peptide or BBK32-induced superfibronectin into contact with plasma fibronectin or into contact with a cell or with tissue comprising the same that is representative of a pathophysiological condition associated with borrelioses or an endothelial cell proliferative disease or disorder. In vitro or ex vivo this is achieved by exposing the plasma fibronectin or cells or tissue in a suitable medium to the BBK32 peptide or BBK32-induced superfibronectin. For in vivo applications, any known method of administration is suitable as described herein.

As used herein, the term "subject" refers to any target of the treatment, preferably a mammal, more preferably a human.

The present invention provides recombinant peptides of the lipoprotein BBK32 from the bacterium *Borrelia burgdorferi* effective to induce superfibronectin (sFN) aggregation in a manner similar to that with the peptide Anastellin. The recombinant BBK32 peptides have biological activities similar to Anastellin in that both proteins can affect the structure of fibronectin matrices formed by cultured fibroblasts and effectively inhibit endothelial cell proliferation. The recombinant BBK32 peptides induce the formation of fibronectin aggregates that are structurally and functionally indistinguishable from Anastellin-induced superfibronectins (sFn).

Particularly, the BBK32 peptides may include a sufficient sequence of residues from the anti-proliferation active site between residues 146 and 175. Preferably, the recombinant BBK32 peptides of the present invention include, but are not limited to, BBK32$_{(21-205)}$, BBK32$_{(21-354)}$, BBK32$_{(153-175)}$, and BBK32$_{(175-202)}$. More preferably, the peptide is BBK32$_{(21-205)}$. Most preferably, the peptide is BBK32$_{(153-175)}$. Alternatively, the BBK32 protein may be used in the present invention. The recombinant peptides may be produced via standard molecular biological techniques or may be chemically synthesized using methods known and standard in the art.

The present invention provides methods of inducing formation of a superfibronectin (sFn) that is conformationally distinct from plasma fibronectin and matrix fibronectin. As such BBK32 protein or the peptides disclosed herein binds to plasma fibronectin and causes compact plasma fibronectin to change conformation. The change in conformation forms insoluble fibronectin aggregates that resemble, but are distinct from matrix fibronectin. Thus, BBK32-induced sFN is produced by contacting plasma fibronecting with the BBK32 protein or BBK32 peptides.

The BBK32-induced sFn is effective to inhibit proliferation of endothelial cells. As such, the present invention provides methods of therapeutic treatment of diseases and disorders having an endothelial cell proliferative component by administering a pharmacologically effective amount of BBK32 protein or BBK32 peptides to induce formation of the antiproliferative superfibronectin. For example, the BBK32 peptides may be pharmacologically effective to treat borrelioses, such as, but not limited to, Lyme disease. Also, the BBK32 peptides may be effective in reducing or halting angiogenesis in a tumor and/or halting or reducing malignant or benign neoplastic cell growth, such as in a cancer. In addition, without being limiting, endothelial cell proliferation may be reduced or halted in pathophysiological conditions, such as stent restinosis or diabetic retinopathies. Furthermore, the BBK32 peptides provided herein are therapeutically useful for wound healing treatments. Thus, the BBK32 peptides induce, via the formation of a BBK32-induced superfibronectin, a therapeutic antiangiogenetic effect in these cell proliferative diseases or disorders.

In addition it is contemplated that the BBK32-induced sFn may be isolated and purified by standard methods. Thus, it is also contemplated that the isolated BBK32-induced superfibronectin may be administered as a therapeutic and/or anti-angiogenic. The BBK32-induced superfibronectin also may be useful in the treatment of endothelial cell proliferative diseases and disorders described herein.

Furthermore, the present invention provides pharmaceutical compositions comprising the BBK32 protein or peptides or the BBK32-induced sFn. Dosage formulations of the BBK32 peptides may comprise conventional non-toxic, physiologically or pharmaceutically acceptable carriers or vehicles suitable for the method of administration. Methods of administration are well-known and standard in the art. Determination of dosage of the BBK32 peptides are well within the purview of one of ordinary skill in the art, as are routes of administration for the same. Such determination is based on, at least in part, on the subject's health, the progression or remission of the disease or disorder, the route of administration and the formulation used.

The following examples are given for the purpose of illustrating various embodiments of the invention and are not meant to limit the present invention in any fashion.

Example 1

Proteins

The Anastellin construct was provided by Dr. Paula McKeown-Longo (Albany Medical College). A recombinant Anastellin protein (SEQ ID NO: 1) with a C-terminal His-tag was produced in bacteria and purified (21-22). Recombinant BBK32$_{(21-205)}$ was expressed and purified as described (6). Recombinant $F_3$ modules are $^1F_3$ (SEQ ID NO: 2), $^{1-2}F_3$ (SEQ ID NO: 3) and $^3F_3$ (SEQ ID NO: 4) were expressed with N-terminal His-tags and purified by standard Ni-NTA and ion-exchange chromatography. FnbpA peptide D3 was synthesized and purified by HPLC using previously described methods (23). Plasma fibronectin was affinity purified from human plasma (Gulf Coast Regional Blood Center Houston, Tex.) as described previously (24).

Anastellin, fibronectin and BBK32 sequences

| Protein/Peptide | Sequence |
| --- | --- |
| Recombinant Anastellin (SEQ ID NO: 1) | NAPQPSHISKYILRWRPKNSVGRWKE ATIPGHLNSYTIKGLKPGVVYEGQLI SIQQYGHQEVTRFDFTTTSTSP |
| $^1F_3$ (SEQ ID NO: 2) | SSGPVEVFITETPSQPNSHPIQWNAP QPSHISKYILRWRPKNSVGRWKEATI PGHLNSYTIKGLKPGVVYEGQLISIQ QYGHQEVTRFDFTTT |
| $^{1-2}F_3$ (SEQ ID NO: 3) | SSGPVEVFITETPSQPNSHPIQWNAP QPSHISKYILRWRPKNSVGRWKEATI PGHLNSYTIKGLKPGVVYEGQLISIQ QYGHQEVTRFDFTTTSTSTPVTSNTV TGETTPFSPLVATSESVTEITASSFV VSWVSASDTVSGFRVEYELSEEGDEP QYLDLPSTATSVNIPDLLPGRKYIVN VYQISEDGEQSLILSTSQTT |
| $^3F_3$ (SEQ ID NO: 4) | APDAPPDPTVDQVDDTSIVVRWSRPQ APITGYRIVYSPSVEGSSTELNLPET ANSVTLSDLQPGVQYNITIYAVEENQ ESTPVVIQQETTG |
| BBK32 (21-354) (SEQ ID NO: 5) | DLFIRYEMKEESPGLFDKGNSILETS EESIKKPIKKPMNKKGKGKIARKKGK SKVSRKEPYIHSLKRDSANKSNFLQK NVILEEESLKTELLKEQSETRKEKIQ KQQDEYKGMTQGSLNSLSGESGELEE PIESNEIDLTIDSDLRPKSSLQGIAG SNSISYTDEIEEEDYDQYYLDEYDEE DEEEIRLSNRYQSYLEGVKYNVDSAI QTITKIYNTYTLFSTKLTQMYSTRLD NFAKAKAKEEAAKFTKEDLEKNFKTL LNYIQVSVKTAANFVYINDTHAKRKL ENIEAEIKTLIAKKIEQSNLYEAYKA IVTSILLMRDSLKEVQGIIDKNGVWY |
| BBK32 (21-205) (SEQ ID NO: 6) | DLFIRYEMKEESPGLFDKGNSILETS EESIKKPIKKPMNKKGKGKIARKKGK SKVSRKEPYIHSLKRDSANKSNFLQK NVILEEESLKTELLKEQSETRKEKIQ KQQDEYKGMTQGSLNSLSGESGELEE PIESNEIDLTIDSDLRPKSSLQGIAG SNSISYTDEIEEEDYDQYYLDEYDEE DEEEIRL |
| BBK32 (146-166) (SEQ ID NO: 7) | EPIESNEIDLTIDSDLRPKSS |
| BBK32 (153-166) (SEQ ID NO: 8) | IDLTIDSDLRPKSS |

-continued

Anastellin, fibronectin and BBK32 sequences

| Protein/Peptide | Sequence |
|---|---|
| BBK32 (153-175) (SEQ ID NO: 9) | IDLTIDSDLRPKSSLQGIAGSNS |
| BBK32 (175-202) (SEQ ID NO: 10) | SISYTDEIEEEDYDQYLDEYDEED EEE |
| BBK32 (160-186) (SEQ ID NO: 11) | DLRPKSSLQGIAGSNSISYTDEIE EED |

ELISA-Type Binding Assay

Binding of BBK32 to $F_3$ modules was tested by coating 1 µg of recombinant $^1F_3$, $^{1-2}F_3$, and $^3F_3$ modules in 50 µl of 50 mM Tris-HCl, 150 mM NaCl, pH 7.5 (TBS) per well in Immulon 4HBX microtiter plates (Dynatech Laboratories, Chantilly, Va.) and incubating overnight at 4° C. The next day, the wells were washed with 200 µl TBS, 0.05% Tween 20, pH 7.4 (TBST) and blocked with 200 µl TBST containing 2% ovalbumin (Sigma, St. Louis, Mo.) for one hour at room temperature. The wells were then washed and BBK32$_{(21-205)}$ or peptide D3 from FnbpA was added to the wells in increasing concentrations. Plates were incubated for one hour at room temperature. After washing with TBST, primary antibodies (rabbit IgG anti-BBK32 or rabbit IgG anti-FnbpA) were added to each well at a 0.48 µg/ml. Plates were incubated for one hour at room temperature and then were washed again with TBST.

Following washing, a 1:3000 dilution of HRP-conjugated goat-anti-rabbit antibodies (BioRad, Hercules, Calif.) was added to each well. Plates were incubated for one hour at room temperature and then washed with TBST. Color was developed by adding SigmaFast™ OPD (Sigma) to each well and incubating at room temperature for 10 minutes. Absorbance was measured at 450 nm using a Thermo Max microplate reader (Molecular Devices, Sunnyvale, Calif.). Apparent Kds were calculated by assessing maximal half-binding $(Y=B_{max} \cdot X/(K_d+X))$.

Fibronectin Aggregation Assay

BBK32, FnbpA peptide D3, Anastellin, and purified plasma fibronectin were centrifuged at 14,000 rpm for 15 minutes and then filtered through 0.22 µm PES syringe filters (Nalgene, Rochester, N.Y.). Following filtration, BBK32, FnbpA peptide D3, and Anastellin were titrated into 1 µM purified plasma fibronectin in TBS. After the addition of each aliquot, the fibronectin/protein mixture was carefully mixed five times with a 200 µl pipette and optical density at 600 nm was measured using a BioPhotometer (Eppendorf, New York, N.Y.) after 10 seconds.

Proteolytic Digestion of Fibronectin Aggregates

BBK32, Anastellin, and plasma fibronectin were dialyzed into thermolysin digestion buffer (25 mM Tris, 0.5 mM EDTA, pH 8, 50 mM NaCl, and 2.5 mM CaCl$_2$). 20 µM BBK32 or 20 µM Anastellin was added to 1 µM plasma fibronectin. Solutions were mixed and aggregates were allowed to form for one hour at room temperature. After one hour incubation, 5 µg/ml thermolysin (Sigma) was added to the BBK32-sFn, the Anastellin-sFn, and to plasma fibronectin. The solutions were incubated at room temperature with end-over-end mixing for 2 hours. Digestion was stopped after two hours with the addition of EDTA to a final concentration of 5 mM. Samples were then run on 4-20% gradient SDS-PAGE gels under non-reducing conditions. Protein fragments were then transferred to PVDF (Millipore, Billerica, Mass.) and stained with Coomassie (40% methanol, 0.25% Brilliant blue-250) until bands were visible. Excess stain was removed with 40% methanol and bands that were present in BBK32-sFn and Anastellin-sFn, but not in plasma fibronectin lanes, were excised and analyzed by N-terminal sequencing using Edman degradation (Protein Sequencing Division, Tufts University Core Facility, Boston, Mass.).

BBK32 Effects on Fibronectin Matrix Assembled by Normal Human Dermal Fibroblasts $4 \times 10^4$ adult normal human dermal fibroblasts (NHDFs) (Cambrex, East Rutherford, N.J.) were seeded onto glass coverslips in 24 well Costar tissue culture plates in Fibroblast growth media-2 (FGM-2) (Cambrex). Cells were allowed to grow for 48 hours and then BBK32, Anastellin, or FnbpA peptide D3 was added to a final concentration of 5 µM in FGM-2. Treated cells were incubated for 20 hours at 37° C., 5% CO$_2$. After incubation, cells were washed with Dulbecco's PBS (DPBS) (Gibco, Invitrogen, Carlsbad, Calif.) and fixed with 2% paraformaldehyde for 30 minutes at room temperature. Following washing with DPBS, cells were blocked with 1% BSA for one hour at room temperature. Cells were then probed with Alexa Fluor 488-anti-fibronectin, Texas Red anti-His, monoclonal antibodies IST-1 (plasma and cellular fibronectin) and IST-9 (cellular fibronectin) (abcam, Cambridge, UK) or combinations of antibodies at a dilution of 1:3000 for one hour at room temperature. Following extensive washing with DPBS, appropriate fluorescently labeled secondary antibodies (Alexa Fluor 594-goat anti-mouse) (Invitrogen, Carlsbad, Calif.) were added at a dilution of 1:3000 and incubated for one hour at room temperature. After incubation, cells were washed extensively with DPBS and coverslips were mounted using Gel/Mount (biømeda, Foster City, Calif.) onto glass slides and images were taken using a LSM 510 Confocal Microscope (Zeiss).

Endothelial Cell Proliferation Assay $1 \times 10^4$ human umbilical vein endothelial cells (HUVECs) (Cambrex) were seeded into Costar 24 well tissue culture plates in endothelial growth media-2 (EGM-2) (Cambrex) and allowed to adhere for two hours. After two hours, BBK32, Anastellin, and FnbpA peptide D3 were added in a dose dependent manner (triplicate) to the wells suspended in EGM-2. Cells were allowed to incubate for 72 hours at 37° C., 5% CO$_2$. After 72 hours, wells were washed with PBS and cells were trypsinized with 0.5% trypsin/EDTA (Cambrex). Trypsinized cells were collected in microcentrifuge tubes and trypsin/EDTA was neutralized with EGM-2. Cells were counted from each well (three counts/well, three wells/dose) using a hemacytometer.

Example 2

BBK32 Binds to $^{1-3}F_3$ in Fibronectin

BBK32 binds to the $^1F_1$-$^5F_1$ N-terminal segment of fibronectin by the tandem beta-zipper mechanism (6-7). Experiments designed to further define the MSCRAMM binding sites in fibronectin by probing a thermolysin digest of fibronectin with BBK32$_{(21-205)}$ in Far Western blots indicated that the MSCRAMM binds more strongly to the 56 kDa fragment than to the 45 kDa gelatin binding fragment. Since the only difference between these two fibronectin fragments is the inclusion of $^1F_3$ in the 56 kDa fragment, this result suggests that BBK32$_{(21-205)}$ may interact with the $^1F_3$ module.

Figure 1A:
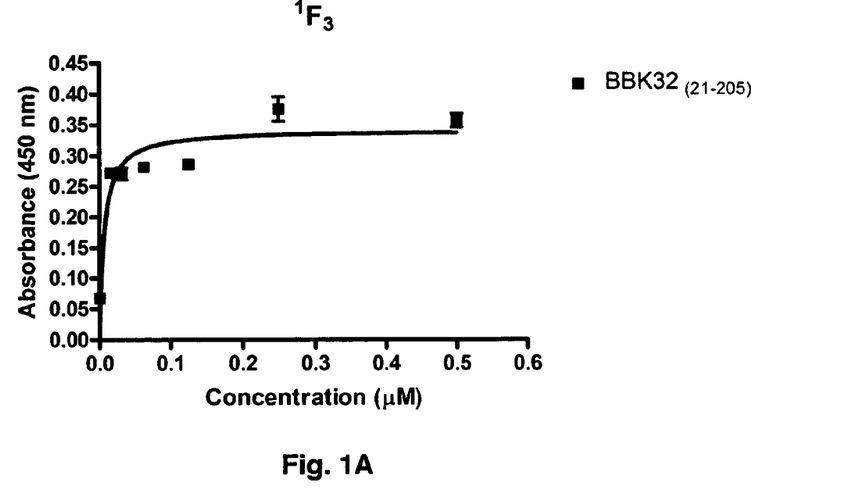
FIGS. 1A-1C demonstrate that $BBK32_{(21-205)}$ binds $F_3$ Modules. Binding to $^1F_3$ (FIG. 1A), $^{1-2}F_3$ (FIG. 1B), and $^3F_3$ (FIG. 1C) was assessed using ELISA-type assays. $F_3$ modules were immobilized in microtiter wells and blocked with Ovalbumin. $BBK32_{(21-205)}$ or FnbpA peptide D3 (*S. aureus* fibronectin-binding peptide) was added to wells in a dose dependent manner. Anti-His antibody followed by HRP conjugated anti-mouse antibody was used to demonstrate binding.
Figure 1B:
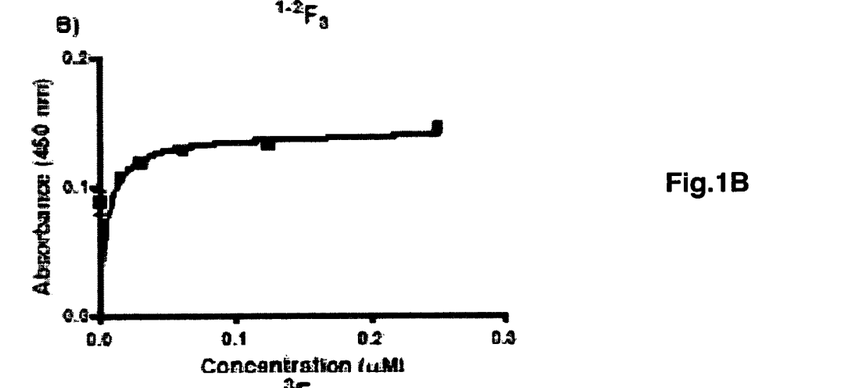
Figure 1C:
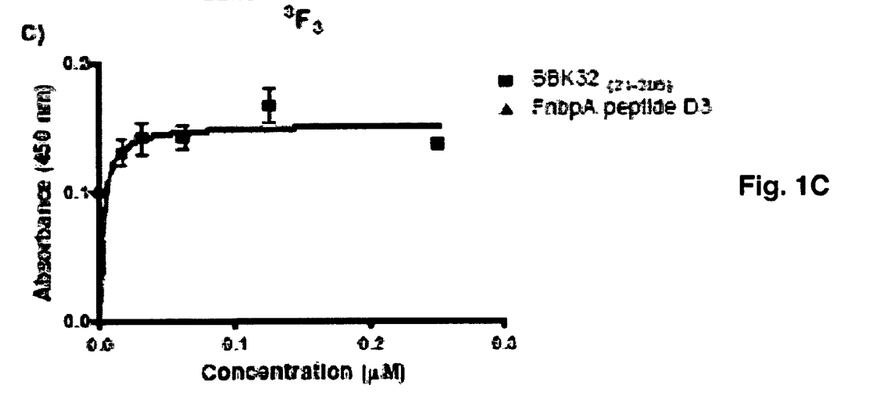

Pure recombinant forms of $^1F_3$, $^{1-2}F_3$, and $^3F_3$ were generated and examined the binding of BBK32 to these fibronectin modules was examined in an ELISA-type binding assays. BBK32 bound all three $F_3$ modules in concentration dependent processes. The binding to the $^1F_3$ module was specific to BBK32 as the D3 fragment of *S. aureus* FnbpA, which has a high affinity for $^1F_1$-$^5F_1$, did not to bind the $^1F_3$ module (FIGS. 1A-1C). The apparent $K_d$ values for the binding of BBK32$_{(21-205)}$ to the $F_3$ containing segments were calculated since all three interactions showed well defined saturation kinetics. These $K_d$ values were all in the low nanomolar range (4.4 nM, 5.6 nM, and 2.5 nM for $^1F_3$, $^{1-2}F_3$, and $^3F_3$ respectively), indicating that this interaction exhibits high specificity.

Example 3

BBK32 Aggregates Plasma Fibronectin in a Concentration Dependent Manner

Figure 2A:
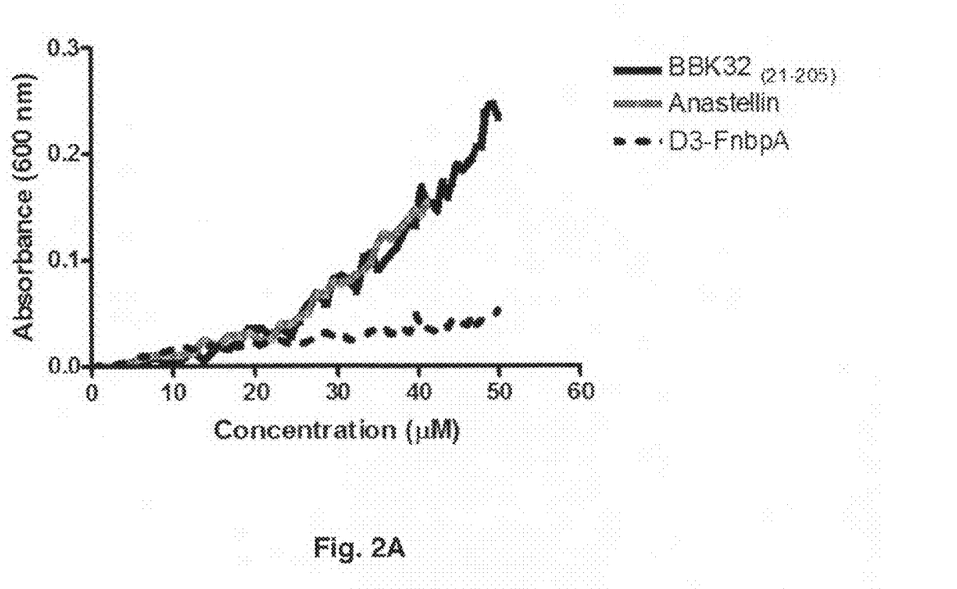
FIGS. 2A-2B illustrate that $BBK32_{(21-205)}$ and $BBK32_{(153-175)}$ aggregate plasma fibronectin. $BBK32_{(21-205)}$, FnbpA peptide D3, and Anastellin (FIG. 2A) or $BBK32_{(21-205)}$, and $BBK32_{(21-354)}$ (FIG. 2B) were titrated into 1 µM purified plasma fibronectin and the optical density at 600 nm (O.D.$_{600}$) was measured.
Figure 2B:
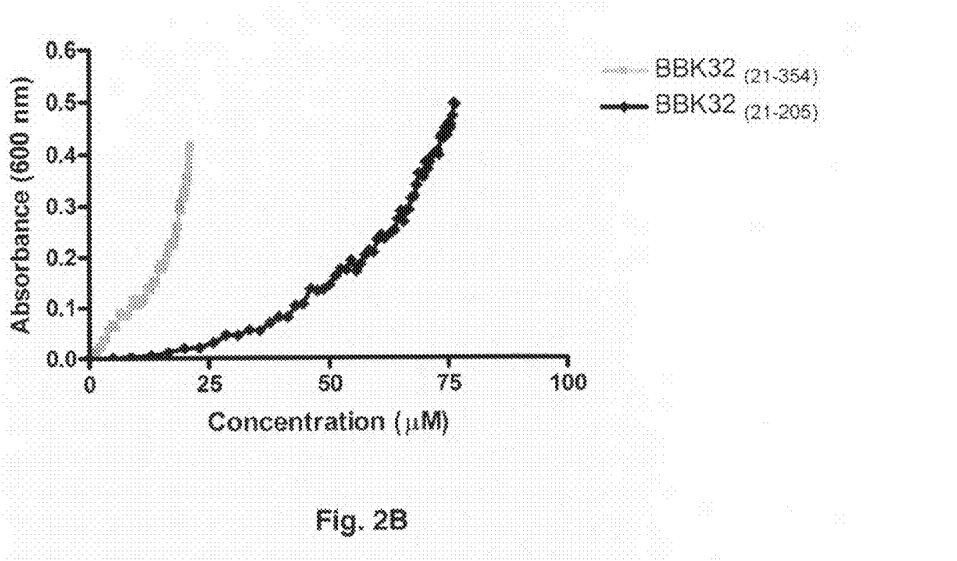

The interaction of BBK32$_{(21-205)}$ with $^1F_3$ and $^3F_3$ is particularly interesting since Anastellin, the only known inducer of sFn, also binds to these modules (25). This similarity raises the possibility that BBK32 can induce an ordered form of fibronectin aggregation. To test this possibility 1 μM of purified plasma fibronectin was incubated with increasing concentrations of BBK32$_{(21-205)}$, Anastellin, or the FnbpA D3 fragment. BBK32 and Anastellin, but not the D3 protein induced fibronectin aggregation that could be followed by the increase in absorbance at 600 nm (FIG. 2A). Fibronectin aggregation was dependent on the concentration of the inducer, and Anastellin and BBK32$_{(21-205)}$ showed very similar activity with aggregation initiated at 20 μM or above. Aggregation of fibronectin was also observed with full length BBK32, which includes the C-terminal globular domain (residues 21-354) (FIG. 2b). BBK32$_{(21-354)}$ induced aggregation of fibronectin at lower concentrations than BBK32$_{(21-205)}$. However, since the longer form of BBK32 is unstable and susceptible to degradation, we used recombinant BBK32$_{(21-205)}$ to further characterize BBK32-dependent Fn aggregation.

Addition of a detergent, Triton X-100, inhibited fibronectin aggregation by BBK32 (not shown) as was previously reported for Anastellin induced fibronectin aggregation (19). When plasma fibronectin is induced to aggregate by Anastellin the protein apparently undergoes conformational changes. These changes involve exposure of cryptic thermolysin cleavage sites which result in unique fragments generated by enzymatic digestion (19). To determine if BBK32 elicits the same effect, purified plasma fibronectin and fibronectin aggregates induced by Anastellin or BBK32$_{(21-205)}$ were digested with thermolysin and the resulting peptides were fractionated by SDS-PAGE.

Figure 3:
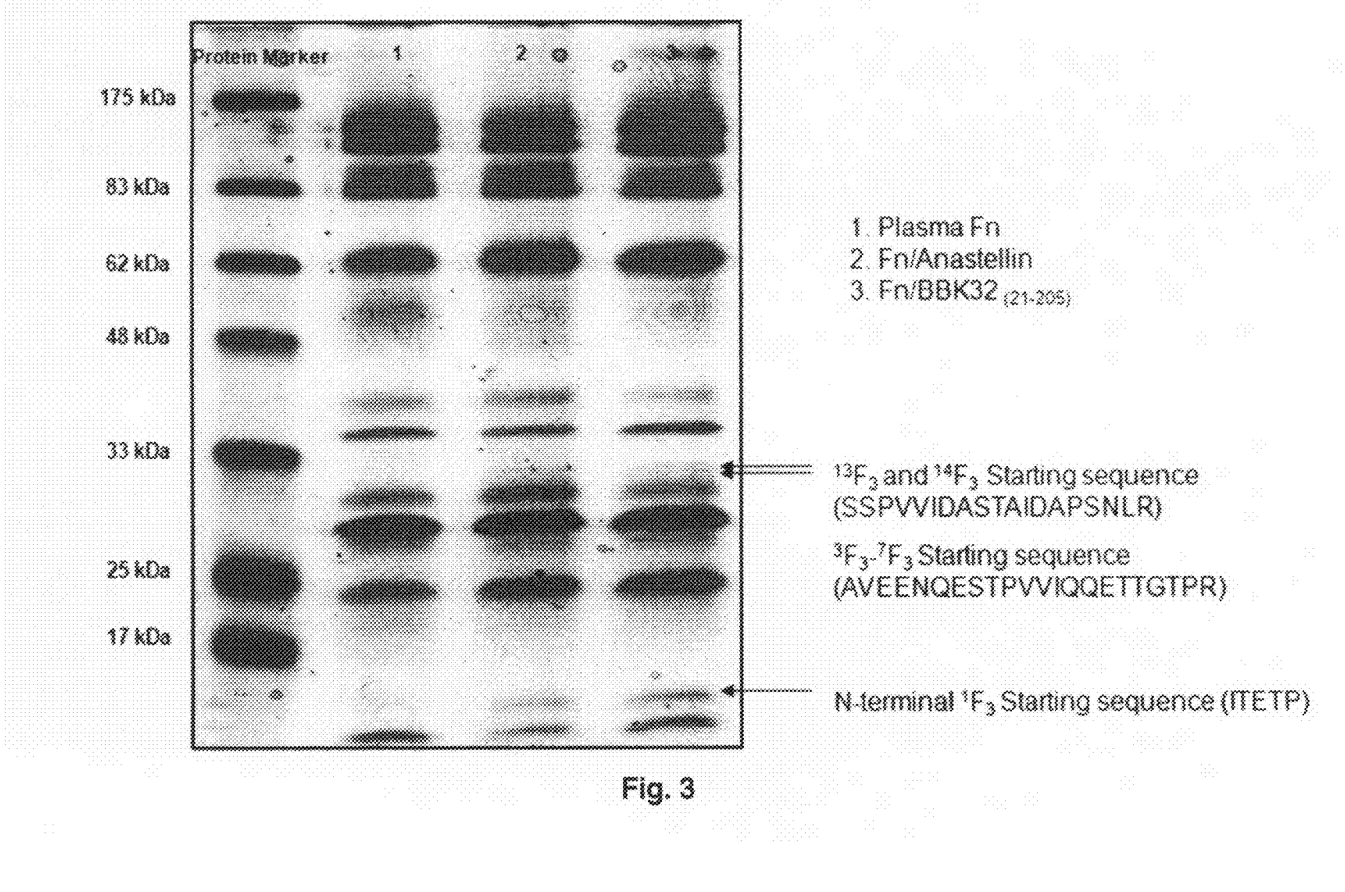
FIG. 3 illustrates that $BBK32_{(21-205)}$ induces a conformational change in plasma fibronectin. Purified plasma fibronectin and fibronectin aggregates induced by Anastellin or $BBK32_{(21-205)}$ were digested with thermolysin. The digested products were fractionated by SDS-PAGE and peptides that were only found in $BBK32_{(21-205)}$/fibronectin (lane 3) or Anastellin/fibronectin (lane 2) digests and not present among the peptides obtained from purified plasma fibronectin (lane 1) were excised and identified by N-terminal sequencing. The sequences obtained, SSPVVID (SEQ ID No. 12), AVEENQE (SEQ ID No. 13), and ITETIP (SEQ ID No. 14), were located to the end of $^{13}F_3$, middle of $^3F_3$, and the start of $^1F_3$, respectively for both BBK32/fibronectin and Anastellin/fibronectin. Pre-stained protein standard (New England Biolabs).

As seen in FIG. 3, fibronectin aggregates induced by Anastellin or BBK32 showed very similar fragment profiles. Furthermore, some peptides are uniquely found in the BBK32$_{(211-205)}$/fibronectin or Anastellin/fibronectin digests and not present among the peptides obtained from purified plasma fibronectin. The bands indicated by arrows in the SDS-PAGE (and equivalent sites from the plasma fibronectin lanes) were excised and subjected to N-terminal sequencing. The sequences obtained, SSPVVID (SEQ ID NO: 12), AVEENQE (SEQ ID NO: 13), and ITETIP (SEQ ID NO: 14), were located at the end of $^{13}F_3$, the middle of $^3F_3$, and near the N-terminus of $^1F_3$. It is contemplated that aggregation of plasma fibronectin by BBK32 or Anastellin involves similar types of conformational changes in the glycoprotein and that these conformational changes are not limited to the $^{1-3}F_3$ region but extend towards the C-terminus of the protein.

Example 4

BBK32 Affects Fibronectin Matrix Assembly

Figure 4A:
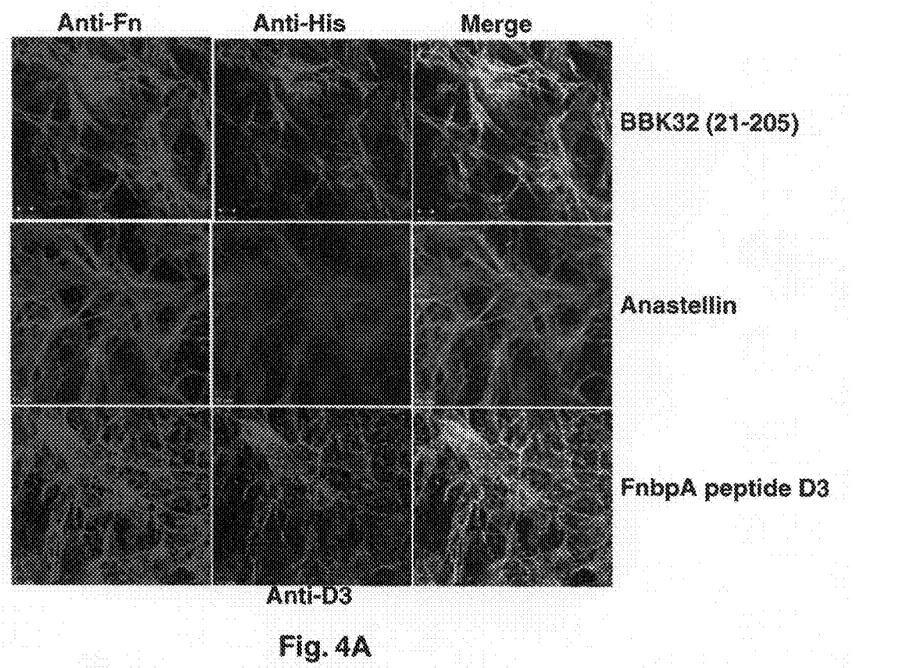

The addition of BBK32 or Anastellin to fibroblast cultures results in the incorporation of the exogenous proteins into the extracellular matrix formed by the cultured cells. Both BBK32, anastellin and FnbpA peptide D3 co-localize with fibronectin in the extracellular matrix of normal human dermal fibroblasts (FIG. 4A). At low concentrations (less than 5 μM), Anastellin has been shown to promote fibronectin matrix assembly, but at high concentrations (above 20 μM), the protein blocks matrix assembly and following a 16 hour incubation, can cause the disappearance of a pre-existing fibronectin matrix (17, 26-27). However, there is some controversy regarding the inhibition and loss of fibronectin matrix after treatment with Anastellin. Klein et al. demonstrated that high concentrations of Anastellin only caused the loss of an epitope in the Extra Domain A (EDA), but otherwise had no effect on the fibronectin matrix after 1-2 hours (28).

The interaction of Anastellin and fibronectin results in conformational changes in cellular fibronectin that can be observed using a monoclonal antibody specific to the alternatively spliced EDA. EDA is only expressed in cellular fibronectin and is upregulated during embryogenesis, wound healing, and tumor progression. Monoclonal antibody IST 9, which is specific for an epitope found on EDA (29), does not recognize cellular fibronectin in the presence of Anastellin (28). IST 9 targets residues 39PEDGIHELFP48 (SEQ ID No. 15) found in the C-C' loop of EDA. It is possible that binding of anastellin to fibronectin induces a conformational change in EDA resulting in the reduction of IST 9 recognition.

Figure 4B:
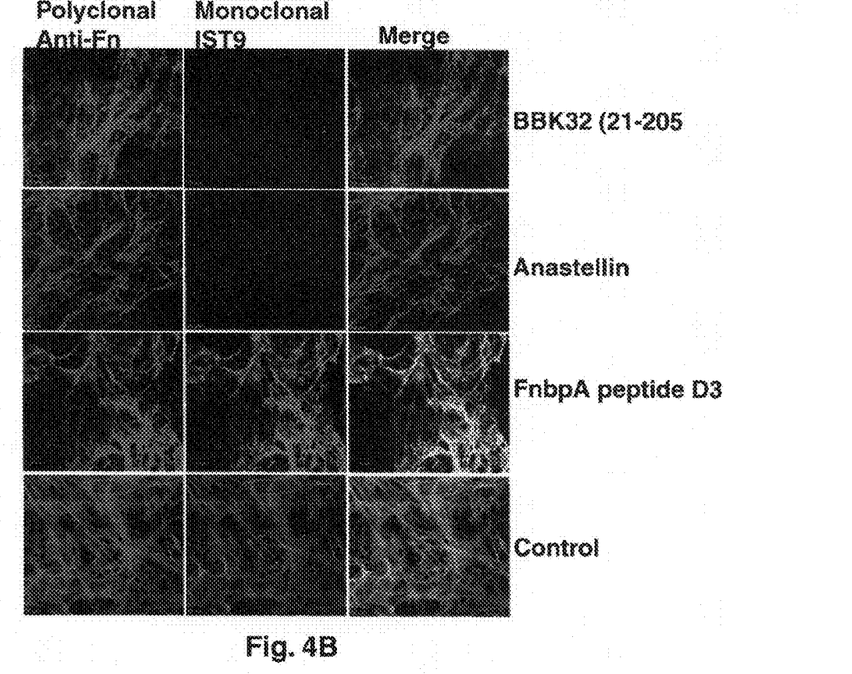

As seen in FIG. 4B, the addition of Anastellin (5 μM) to cultured normal human dermal fibroblasts results in markedly reduced immunostaining with IST 9 (FIG. 4B). Addition of BBK32 (5 μM) also results in a reduction of immunostaining with IST 9. The D3 fragment of FnbpA was used as a control. IST 9 staining of D3 treated cells was no different from the staining observed for the no treatment control (FIG. 4B). Polyclonal anti-fibronectin and monoclonal IST 1, which recognizes an epitope in $^{12}F_3$, were used to demonstrate the presence of fibronectin in BBK32 or Anastellin treated matrices. A reduction in immunostaining with IST 9 indicates that BBK32 may alter the conformation of cellular fibronectin in a manner similar to that seen with anastellin.

Example 5

BBK32 Inhibits the Proliferation of Cultured Endothelial Cells

Figure 5A:
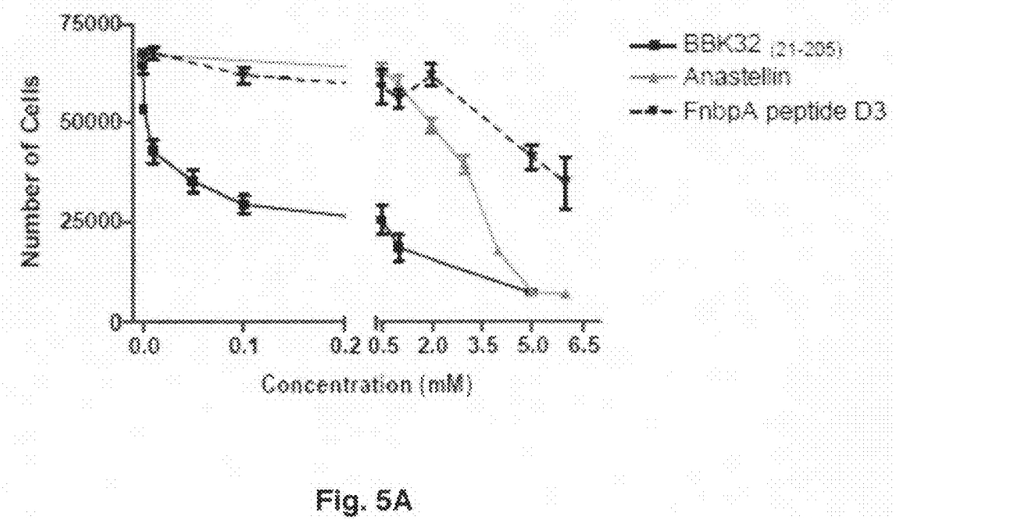
FIGS. 5A-5B illustrate that $BBK32_{(21-205)}$ and $BBK32_{(153-175)}$ inhibit the proliferation of HUVECs. Cells were seeded onto tissue culture plates in full media and allowed to adhere for two hours. After two hours, $BBK32_{(21-205)}$, Anastellin, and FnbpA peptide D3 (FIG. 5A) or $BBK32_{(21-205)}$, $BBK32_{(153-175)}$, $BBK32_{(175-202)}$, and Anastellin (FIG. 5B) were added in a dose dependent manner (in triplicate) to the wells suspended in media. Cells were then incubated for 72 hours at 37° C., 5% $CO_2$. After 72 hours, wells were washed, trypsinized, and counted (three counts/well, three wells/dose) using a hemacytometer.
Figure 5B:
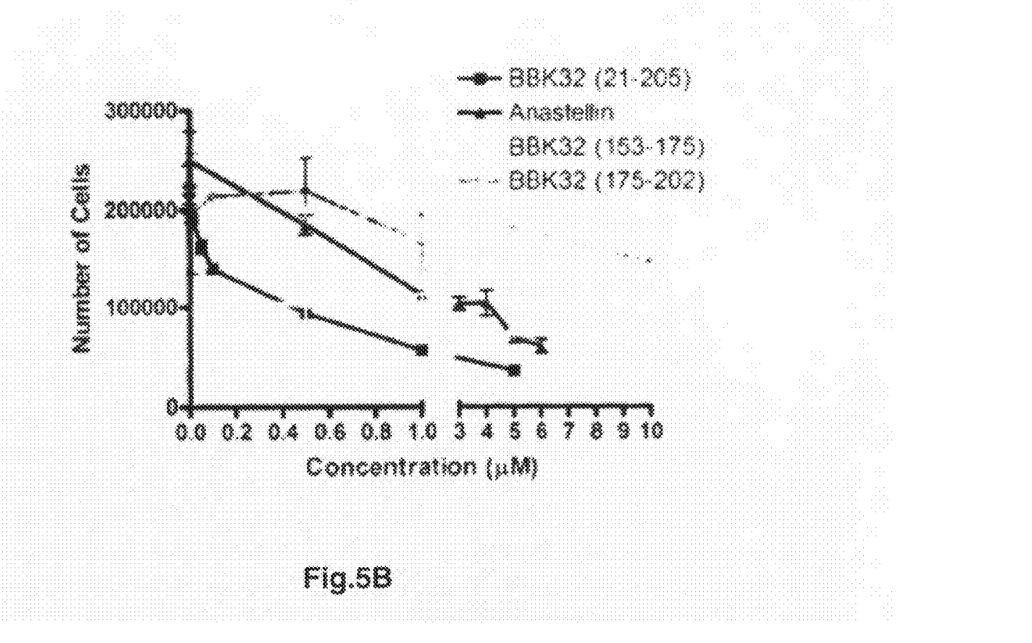

The ability of Anastellin to inhibit endothelial cell proliferation is one of its most prominent activities (21, 30-31). Since BBK32 behaves like Anastellin in its interaction with fibronectin, the ability of BBK32 to affect proliferation of human umbilical vein endothelial cells was examined (FIGS. 5A-5B). Anastellin and the D3 fragment of FnbpA were used as controls.

FIG. 5A shows that BBK32 inhibited the proliferation of endothelial cells in a concentration dependent manner as observed for Anastellin. Surprisingly, BBK32 was reproducibly more potent at inhibiting endothelial cell proliferation than Anastellin. The decrease in proliferation was observed at 24 and 48 hours (data not shown), but was more pronounced following 72 hours of static culture. The FnbpA peptide D3 only marginally affected the proliferation of cells. The inhibition of endothelial cell proliferation was apparently not due to apoptosis since Annexin V assays were negative (not shown). Recently, it was demonstrated that anastellin inhibits endothelial cell proliferation by causing G1 arrest (30). Since BBK32 does not induce apoptosis and there is no evidence of cell death, it is contemplated that the BBK32-dependent inhibition of endothelial cell proliferation may also be due to cell cycle arrest.

FIG. 5B shows that the anti-proliferation active site in BBK32 lies between residues 146 and 175. BBK32 peptides, $BBK32_{(21-205)}$, $BBK32_{(153-175)}$ and $BBK32_{(175-202)}$, and Anastellin, as control, were added to human umbilical vein endothelial cells, as described.

A Motif in BBK32 Responsible for the Superfibronectin Formation Activity

Sequence alignment of BBK32 and anastellin indicate two regions of sequence similarity. Both motifs are located in BBK32 peptide 153-175. $BBK32_{(153-175)}$ was assessed in the aggregation assay, monoclonal antibody IST 9 conformational change assay, and the endothelial cell proliferation assay. The peptide was found to induce aggregation of plasma fibronectin in a concentration dependent manner. IST 9 monoclonal antibody immunostaining of $BBK32_{(153-175)}$-induced sFn indicates conformational changes in fibronectin in matrices produced by fibroblasts. $BBK32_{(153-175)}$ inhibits human umbilical vein endothelial cell proliferation in a concentration dependent manner.

sFn May Affect Transendothelial Migration

Leukocytes and endothelial cells express a4b1 integrins on their cell surfaces. $a_4b_1$ integrins bind to intercellular cell adhesion molecules (ICAM) and vascular cell adhesion molecules (VCAM). ICAM and VCAM are expressed on the surface of endothelial cells and are involved in the formation and maintenance of tight junctions in the endothelium. SFn formation due to BBK32 on or near the surface of the endothelium could cause a decrease in transendothelium migration by leukocytes that are being recruited to the infection site. This could occur through the enhanced binding of $a_4b_1$ integrins on the leukocytes to the sFn matrix. Essentially, the leukocytes could get trapped in the matrix.

To determine if sFn decrease the migration of leukocytes to the infection site, transendothelial migration assays were assessed. In these assays endothelial cells were grown to confluence in Transwell® inserts and were encouraged to form tight junctions using interleukin 4 (IL-4). SFn formation was then induced to form on the surface of the endothelial cell layer using BBK32 (21-354), (21-205) and (153-175). A chemoattractant (IL-8) was added to the bottom chamber of the Transwell setup. Mononuclear cells were added to the upper chamber and permitted to migrate for four hours. Following incubation, cells in the bottom chamber were counted.

A decrease in the number of leukocytes found in the bottom chamber of the Transwell with sFn compared to no sFn, indicates that BBK32-induced sFn could be used by the spirochete to prevent recruitment of immune cells to the infection site. sFn produced by the identified sFn-inducing BBK32 peptide (153-175) is as effective at inhibiting transendothelial migration as the full length BBK32 protein.

The *B. burgdorferi* lipoprotein BBK32 was previously shown to bind to the N-terminal $^1F_1$-$^5F_1$ segment of fibronectin through a tandem beta-zipper mechanism. The present invention demonstrates that a recombinant form of BBK32 (21-205) also binds to fibronectin F3 modules and can induce an ordered fibronectin aggregation that resembles the formation of sFn induced by anastellin. This aggregation probably is a consequence of conformational changes induced in fibronectin upon BBK32 or anastellin binding. Aggregates of plasma fibronectin induced by either BBK32 or anastellin expose similar thermolysin cleavage sites. Both proteins affect the structure of cellular fibronectin in deposited matrices by cultured fibroblasts as monitored by the disappearance of the epitope for the monoclonal antibody IST9. Furthermore, both BBK32 and anastellin can inhibit the proliferation of cultured endothelial cells. Thus, BBK32 and anastellin appear to modulate the conformation of fibronectin in similar ways and have similar biological activities. A segment of the staphylococcal fibronectin-binding MSCRAMM FnbpA did not show these effects. The FnbpA D3 segment contains a well defined $^4F_1$-$^5F_1$ and $F_3$ binding motif, but does not bind to F3 modules nor does it induce fibronectin aggregation. These results show that the induction of sFn formation described here for BBK32 is not common to all fibronectin-binding MSCRAMMs. In fact, other bacterial proteins or MSCRAMMs that can induce an ordered fibronectin aggregation are unknown.

Recombinant anastellin and BBK32 are structurally different. Anastellin represents the C-terminal two-thirds of the fibronectin $^1F_3$ module, and has a defined structure with two b-sheets. The fibronectin interacting region of BBK32 (residues 21-205) corresponds to an intrinsically disordered segment of the MSCRAMM. Although most of the experiments reported in this communication were performed with the recombinant fragment of BBK32 encompassing the fibronectin-binding sites, it was shown that a recombinant version of the intact BBK32 protein (residues 21-354) was an even more powerful sFn inducer. Therefore, it is also possible that BBK32 expressed on the surface of the spirochete can induce sFn formation and that this activity can play a role in the pathogenesis of borrelioses.

It is tempting to speculate that BBK32 binding to F3 modules and inducing sFn formation provides additional advantages to the spirochete during the infection. What these advantages might be are unclear. The ability of BBK32 to inhibit endothelial cell proliferation may ultimately facilitate the hematogenous spread of the spirochetes that are initially deposited locally at the tick bite site. During this process the spirochetes are believed to cross the endothelial lining twice, once to enter the blood stream and once to exit. Inhibiting endothelial cell proliferation at the wound site could facilitate this process. It is also intriguing that BBK32 induces a conformational change in cellular fibronectin that can be monitored by the loss of the epitope recognized by the monoclonal antibody IST 9. This epitope has been located to the EDA module (specifically residues 39PEDGIHELFP48) that also harbors binding sites for the $a_4b_1$ and a9 b1 integrins. It is possible that binding of BBK32 to Fn may regulate Fn's interaction with these integrins, which in turn may benefit the spirochetes. Integrin a4b1 interacts with the vascular cellular adhesion molecule (VCAM 1) during leukocyte transendothelial migration. Exposure of the $a_4b_1$ integrin recognition sequence in EDA upon sFn formation may cause leukocytes to adhere to fibronectin, rather than to cross the endothelial cell barrier. Blocking $a_4b_1$ integrins in a mouse model of Lyme arthritis reduces the influx of leukocytes into joints and reduces the production of inflammatory mediators.

The loss of bbk32 from *B. burgdorferi* results in a modest decrease in infectivity. This observation provides strong context for the findings that demonstrate the ability of BBK32 to promote conformational changes in fibronectin to form sFn.

The following references are cited herein:
1. Steere, et al. (2004) *J Clin Invest* 113, 1093-101.
2. Probert, W. S. & Johnson, B. J. (1998) *Mol Microbiol* 30, 1003-15.
3. Fikrig, et al. (2000) *J Immunol* 164, 5344-51.
4. Heikkila, et al. (2002) *J Clin Microbiol* 40, 1174-80.
5. Seshu, et al. (2006) *Mol Microbiol* 59, 1591-601.
6. Kim, et al. (2004) *J Biol Chem* 279, 41706-14.
7. Raibaud, et al. (2005) *J Biol Chem* 280, 18803-9.
8. Schwarz-Linek, et al. (2003) *Nature* 423, 177-81.
9. Mosher, D. F. (1989) *Fibronectin* (Academic Press, Inc., San Diego).
10. Plaxco, et al. (1996) *Proc Natl Acad Sci USA* 93, 10703-6
11. Plaxco, et al. (1997) *J Mol Biol* 270, 763-70.
12. Johnson, et al. (1999) *Jour of Biological Chemistry* 274, 15473-15479.
13. Mao, Y. & Schwarzbauer, J. E. (2005) *Matrix Biology* 24, 389-399.
14. Pankov, et al. (2000) *J Cell Biol* 148, 1075-90.
15. Sechler, et al. (2000) *J Cell Sci* 113 (Pt 8), 1491-8.
16. Tomasini-Johansson, B et al. (2001) *J Biol Chem* 276, 23430-9.
17. Morla, et al. (1994) *Nature* 367, 193-6.
18. Briknarova, et al. (2003) *J Mol Biol* 332, 205-15.
19. Ohashi, T. & Erickson, H. P. (2005) *J Biol Chem* 280, 39143-51.
20. Schwarz-Linek, et al. (2004) *J Biol Chem* 279, 39017-25.
21. Pasqualini, et al. (1996) *Nat Med* 2, 1197-203.
22. Sakai, et al. (2001) *Nat Med* 7, 324-30.
23. McGavin, et al. (1993) *J Biol Chem* 268, 23946-53.
24. Vuento, M. & Vaheri, A. (1979) *Biochem J* 183, 331-7.
25. Ingham, et al. (1997) *J Biol Chem* 272, 1718-24.
26. Bourdoulous, et al. (1998) *J Cell Biol* 143, 267-76.
27. Morla, A. & Ruoslahti, E. (1992) *J Cell Biol* 118, 421-9.
28. Klein, et al. (2003) *J Cell Sci* 116, 4663-74.
29. Carnemolla, et al. (1987) *FEBS Lett* 215, 269-73.
30. Ambesi, et al. (2005) *Cancer Res* 65, 148-56.
31. Yi, M. & Ruoslahti, E. (2001) *Proc Natl Acad Sci USA* 98, 620-4.

Any publications mentioned in this specification are indicative of the levels of those skilled in the art to which the invention pertains. Further, these publications are incorporated by reference herein to the same extent as if each individual publication was specifically and individually incorporated by reference.

One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A method for inducing formation of a superfibronectin, comprising:

contacting plasma fibronectin with at least one BBK32 peptide selected from the list consisting of: $BBK_{(21-354)}$ with the amino acid sequence shown in SEQ ID NO: 5, $BBK_{(21-205)}$ with the amino acid sequence shown in SEQ ID NO: 6, and $BBK_{(153-175)}$ with the amino acid sequence shown in SEQ ID NO: 9; wherein binding of the BBK32 peptide to the plasma fibronectin induces a conformational change therein thereby forming the superfibronectin.

2. The method of claim 1, wherein the BBK32-induced superfibronectin is conformationally distinct from plasma fibronectin and matrix fibronectin.

3. The method of claim 1, further comprising:

inhibiting proliferation of endothelial cells by contacting said endothelial cells with superfibronectin formed by the binding of the BBK32 peptide to plasma fibronectin.

4. The method of claim 3, wherein inhibiting proliferation of the endothelial cells inhibits angiogenesis.

5. The method of claim 3, wherein the endothelial cells are associated with an endothelial cell proliferative pathophysiological condition.

6. The method of claim 5, wherein the pathophysiological condition is a borreliosis, a neoplastic disease, stent restinosis, diabetic retinopathy, or a wound.

7. The method of claim 6, wherein the borreliosis is Lyme disease.

8. The method of claim 1, further comprising:

isolating the BBK32-induced superfibronectin.

* * * * *

```
SEQUENCE LISTING

<160> NUMBER OF SEQ ID NOS: 17

<210> SEQ ID NO 1
<211> LENGTH: 74
<212> TYPE: PRT
<213> ORGANISM: artificial sequence
<220> FEATURE:
<223> OTHER INFORMATION: recombinant anastellin protein

<400> SEQUENCE: 1

Asn Ala Pro Gln Pro Ser His Ile Ser Lys Tyr Ile Leu Arg Trp
1               5                   10                  15

Arg Pro Lys Asn Ser Val Gly Arg Trp Lys Glu Ala Thr Ile Pro
                20                  25                  30

Gly His Leu Asn Ser Tyr Thr Ile Lys Gly Leu Lys Pro Gly Val
                35                  40                  45

Val Tyr Glu Gly Gln Leu Ile Ser Ile Gln Gln Tyr Gly His Gln
                50                  55                  60

Glu Val Thr Arg Phe Asp Phe Thr Thr Thr Ser Thr Ser Pro
                65                  70

<210> SEQ ID NO 2
<211> LENGTH: 93
<212> TYPE: PRT
<213> ORGANISM: artificial sequence
<220> FEATURE:
<223> OTHER INFORMATION: recombinant fibronectin peptide 1F3

<400> SEQUENCE: 2

Ser Ser Gly Pro Val Glu Val Phe Ile Thr Glu Thr Pro Ser Gln
1               5                   10                  15

Pro Asn Ser His Pro Ile Gln Trp Asn Ala Pro Gln Pro Ser His
```

```
                    20                  25                  30

Ile Ser Lys Tyr Ile Leu Arg Trp Arg Pro Lys Asn Ser Val Gly
                35                  40                  45

Arg Trp Lys Glu Ala Thr Ile Pro Gly His Leu Asn Ser Tyr Thr
            50                  55                  60

Ile Lys Gly Leu Lys Pro Gly Val Val Tyr Glu Gly Gln Leu Ile
        65                  70                  75

Ser Ile Gln Gln Tyr Gly His Gln Glu Val Thr Arg Phe Asp Phe
    80                  85                  90

Thr Thr Thr

<210> SEQ ID NO 3
<211> LENGTH: 202
<212> TYPE: PRT
<213> ORGANISM: artificial sequence
<220> FEATURE:
<223> OTHER INFORMATION: recombinant fibronectin peptide 1-3F3

<400> SEQUENCE: 3

Ser Ser Gly Pro Val Glu Val Phe Ile Thr Glu Thr Pro Ser Gln
1               5                   10                  15

Pro Asn Ser His Pro Ile Gln Trp Asn Ala Pro Gln Pro Ser His
                20                  25                  30

Ile Ser Lys Tyr Ile Leu Arg Trp Arg Pro Lys Asn Ser Val Gly
                35                  40                  45

Arg Trp Lys Glu Ala Thr Ile Pro Gly His Leu Asn Ser Tyr Thr
            50                  55                  60

Ile Lys Gly Leu Lys Pro Gly Val Val Tyr Glu Gly Gln Leu Ile
        65                  70                  75

Ser Ile Gln Gln Tyr Gly His Gln Glu Val Thr Arg Phe Asp Phe
    80                  85                  90

Thr Thr Thr Ser Thr Ser Thr Pro Val Thr Ser Asn Thr Val Thr
                95                  100                 105

Gly Glu Thr Thr Pro Phe Ser Pro Leu Val Ala Thr Ser Glu Ser
                110                 115                 120

Val Thr Glu Ile Thr Ala Ser Ser Phe Val Val Ser Trp Val Ser
            125                 130                 135

Ala Ser Asp Thr Val Ser Gly Phe Arg Val Glu Tyr Glu Leu Ser
        140                 145                 150

Glu Glu Gly Asp Glu Pro Gln Tyr Leu Asp Leu Pro Ser Thr Ala
    155                 160                 165

Thr Ser Val Asn Ile Pro Asp Leu Leu Pro Gly Arg Lys Tyr Ile
                170                 175                 180

Val Asn Val Tyr Gln Ile Ser Glu Asp Gly Glu Gln Ser Leu Ile
                185                 190                 195

Leu Ser Thr Ser Gln Thr Thr
                200

<210> SEQ ID NO 4
<211> LENGTH: 91
<212> TYPE: PRT
<213> ORGANISM: artificial sequence
<220> FEATURE:
<223> OTHER INFORMATION: recombinant fibronectin peptide 3F3

<400> SEQUENCE: 4

Ala Pro Asp Ala Pro Pro Asp Pro Thr Val Asp Gln Val Asp Asp
```

```
              1               5                  10                 15
Thr Ser Ile Val Val Arg Trp Ser Arg Pro Gln Ala Pro Ile Thr
                        20                 25                 30

Gly Tyr Arg Ile Val Tyr Ser Pro Ser Val Glu Gly Ser Ser Thr
                        35                 40                 45

Glu Leu Asn Leu Pro Glu Thr Ala Asn Ser Val Thr Leu Ser Asp
                        50                 55                 60

Leu Gln Pro Gly Val Gln Tyr Asn Ile Thr Ile Tyr Ala Val Glu
                        65                 70                 75

Glu Asn Gln Glu Ser Thr Pro Val Val Ile Gln Glu Thr Thr
                        80                 85                 90

Gly

<210> SEQ ID NO 5
<211> LENGTH: 338
<212> TYPE: PRT
<213> ORGANISM: artificial sequence
<220> FEATURE:
<223> OTHER INFORMATION: recombinant peptide from residues 21-354 of
      BBK32

<400> SEQUENCE: 5

Asp Leu Phe Ile Arg Tyr Glu Met Lys Glu Glu Ser Pro Gly Leu
1               5                  10                 15

Phe Asp Lys Gly Asn Ser Ile Leu Glu Thr Ser Glu Glu Ser Ile
                        20                 25                 30

Lys Lys Pro Ile Lys Lys Pro Met Asn Lys Gly Lys Gly Lys Lys
                        35                 40                 45

Ile Ala Arg Lys Lys Gly Lys Ser Lys Val Ser Arg Lys Glu Pro
                        50                 55                 60

Tyr Ile His Ser Leu Lys Arg Asp Ser Ala Asn Lys Ser Asn Phe
                        65                 70                 75

Leu Gln Lys Asn Val Ile Leu Glu Glu Ser Leu Lys Thr Glu
                        80                 85                 90

Leu Leu Lys Glu Gln Ser Glu Thr Arg Lys Glu Lys Ile Gln Lys
                        95                100                105

Gln Gln Asp Glu Tyr Lys Gly Met Thr Gln Gly Ser Leu Asn Ser
                       110                115                120

Leu Ser Gly Glu Ser Gly Glu Leu Glu Glu Pro Ile Glu Ser Asn
                       125                130                135

Glu Ile Asp Leu Thr Ile Asp Ser Asp Leu Arg Pro Lys Ser Ser
                       140                145                150

Leu Gln Gly Ile Ala Gly Ser Asn Ser Ile Ser Tyr Thr Asp Glu
                       155                160                165

Ile Glu Glu Glu Asp Tyr Asp Gln Tyr Tyr Leu Asp Glu Tyr Asp
                       170                175                180

Glu Glu Asp Glu Glu Glu Ile Arg Leu Ser Asn Arg Tyr Gln Ser
                       185                190                195

Tyr Leu Glu Gly Val Lys Tyr Asn Val Asp Ser Ala Ile Gln Thr
                       200                205                210

Ile Thr Lys Ile Tyr Asn Thr Tyr Thr Leu Phe Ser Thr Lys Leu
                       215                220                225

Thr Gln Met Tyr Ser Thr Arg Leu Asp Asn Phe Ala Lys Ala Lys
                       230                235                240

Ala Lys Glu Glu Ala Ala Lys Phe Thr Lys Glu Asp Leu Glu Lys
```

-continued

```
                245                 250                 255

Asn Phe Lys Thr Leu Leu Asn Tyr Ile Gln Val Ser Val Lys Thr
            260                 265                 270

Ala Ala Asn Phe Val Tyr Ile Asn Asp Thr His Ala Lys Arg Lys
            275                 280                 285

Leu Glu Asn Ile Glu Ala Glu Ile Lys Thr Leu Ile Ala Lys Lys
            290                 295                 300

Ile Glu Gln Ser Asn Leu Tyr Glu Ala Tyr Lys Ala Ile Val Thr
            305                 310                 315

Ser Ile Leu Leu Met Arg Asp Ser Leu Lys Glu Val Gln Gly Ile
            320                 325                 330

Ile Asp Lys Asn Gly Val Trp Tyr
            335

<210> SEQ ID NO 6
<211> LENGTH: 189
<212> TYPE: PRT
<213> ORGANISM: artificial sequence
<220> FEATURE:
<223> OTHER INFORMATION: recombinant peptide from residues 21-205 of
      BBK32

<400> SEQUENCE: 6

Asp Leu Phe Ile Arg Tyr Glu Met Lys Glu Ser Pro Gly Leu
1               5                   10                  15

Phe Asp Lys Gly Asn Ser Ile Leu Glu Thr Ser Glu Glu Ser Ile
            20                  25                  30

Lys Lys Pro Ile Lys Lys Pro Met Asn Lys Lys Gly Lys Gly Lys
            35                  40                  45

Ile Ala Arg Lys Lys Gly Lys Ser Lys Val Ser Arg Lys Glu Pro
            50                  55                  60

Tyr Ile His Ser Leu Lys Arg Asp Ser Ala Asn Lys Ser Asn Phe
            65                  70                  75

Leu Gln Lys Asn Val Ile Leu Glu Glu Glu Ser Leu Lys Thr Glu
            80                  85                  90

Leu Leu Lys Glu Gln Ser Glu Thr Arg Lys Glu Lys Ile Gln Lys
            95                  100                 105

Gln Gln Asp Glu Tyr Lys Gly Met Thr Gln Gly Ser Leu Asn Ser
            110                 115                 120

Leu Ser Gly Glu Ser Gly Glu Leu Glu Glu Pro Ile Glu Ser Asn
            125                 130                 135

Glu Ile Asp Leu Thr Ile Asp Ser Asp Leu Arg Pro Lys Ser Ser
            140                 145                 150

Leu Gln Gly Ile Ala Gly Ser Asn Ser Ile Ser Tyr Thr Asp Glu
            155                 160                 165

Ile Glu Glu Glu Asp Tyr Asp Gln Tyr Tyr Leu Asp Glu Tyr Asp
            170                 175                 180

Glu Glu Asp Glu Glu Glu Ile Arg Leu
            185

<210> SEQ ID NO 7
<211> LENGTH: 21
<212> TYPE: PRT
<213> ORGANISM: artificial sequence
<220> FEATURE:
<223> OTHER INFORMATION: recombinant peptide from residues 146-166 of
      BBK32
```

-continued

```
<400> SEQUENCE: 7

Glu Pro Ile Glu Ser Asn Glu Ile Asp Leu Thr Ile Asp Ser Asp
1               5                   10                  15

Leu Arg Pro Lys Ser Ser
            20

<210> SEQ ID NO 8
<211> LENGTH: 14
<212> TYPE: PRT
<213> ORGANISM: artificial sequence
<220> FEATURE:
<223> OTHER INFORMATION: recombinant peptide from residues 153-166 of
      BBK32

<400> SEQUENCE: 8

Ile Asp Leu Thr Ile Asp Ser Asp Leu Arg Pro Lys Ser Ser
1               5                   10

<210> SEQ ID NO 9
<211> LENGTH: 23
<212> TYPE: PRT
<213> ORGANISM: artificial sequence
<220> FEATURE:
<223> OTHER INFORMATION: recombinant peptide from residues 153-175 of
      BBK32

<400> SEQUENCE: 9

Ile Asp Leu Thr Ile Asp Ser Asp Leu Arg Pro Lys Ser Ser Leu
1               5                   10                  15

Gln Gly Ile Ala Gly Ser Asn Ser
            20

<210> SEQ ID NO 10
<211> LENGTH: 27
<212> TYPE: PRT
<213> ORGANISM: artificial sequence
<220> FEATURE:
<223> OTHER INFORMATION: recombinant peptide from residues 175-202 of
      BBK32

<400> SEQUENCE: 10

Ser Ile Ser Tyr Thr Asp Glu Ile Glu Glu Glu Asp Tyr Asp Gln
1               5                   10                  15

Tyr Leu Asp Glu Tyr Asp Glu Glu Asp Glu Glu Glu
            20                  25

<210> SEQ ID NO 11
<211> LENGTH: 27
<212> TYPE: PRT
<213> ORGANISM: artificial sequence
<220> FEATURE:
<223> OTHER INFORMATION: recombinant peptide from residues 160-186 of
      BBK32

<400> SEQUENCE: 11

Asp Leu Arg Pro Lys Ser Ser Leu Gln Gly Ile Ala Gly Ser Asn
1               5                   10                  15

Ser Ile Ser Tyr Thr Asp Glu Ile Glu Glu Glu Asp
            20                  25

<210> SEQ ID NO 12
<211> LENGTH: 7
<212> TYPE: PRT
<213> ORGANISM: artificial sequence
<220> FEATURE:
```

-continued

<223> OTHER INFORMATION: 1-3F3 fibronectin fragment

<400> SEQUENCE: 12

Ser Ser Pro Val Val Ile Asp
1               5

<210> SEQ ID NO 13
<211> LENGTH: 7
<212> TYPE: PRT
<213> ORGANISM: artificial sequence
<220> FEATURE:
<223> OTHER INFORMATION: 3F3 fibronectin fragment

<400> SEQUENCE: 13

Ala Val Glu Glu Asn Gln Glu
1               5

<210> SEQ ID NO 14
<211> LENGTH: 5
<212> TYPE: PRT
<213> ORGANISM: artificial sequence
<220> FEATURE:
<223> OTHER INFORMATION: 1F3 fibronectin fragment

<400> SEQUENCE: 14

Ile Thr Glu Thr Pro
1               5

<210> SEQ ID NO 15
<211> LENGTH: 10
<212> TYPE: PRT
<213> ORGANISM: artificial sequence
<220> FEATURE:
<223> OTHER INFORMATION: epitope residues 39-48 of Extra Domain A of
      fibronectin

<400> SEQUENCE: 15

Pro Glu Asp Gly Ile His Glu Leu Phe Pro
1               5                   10

<210> SEQ ID NO 16
<211> LENGTH: 19
<212> TYPE: PRT
<213> ORGANISM: artificial sequence
<220> FEATURE:
<223> OTHER INFORMATION: 13F3 and 14F3 fibronectin fragment

<400> SEQUENCE: 16

Ser Ser Pro Val Val Ile Asp Ala Ser Thr Ala Ile Asp Ala Pro
1               5                   10                  15

Ser Asn Leu Arg

<210> SEQ ID NO 17
<211> LENGTH: 22
<212> TYPE: PRT
<213> ORGANISM: artificial sequence
<220> FEATURE:
<223> OTHER INFORMATION: 3F3 - 7F3 fibronectin fragment

<400> SEQUENCE: 17

Ala Val Glu Glu Asn Gln Glu Ser Thr Pro Val Val Ile Gln Gln
1               5                   10                  15

Glu Thr Thr Gly Thr Pro Arg
                20